United States Patent
Neu et al.

(10) Patent No.: US 7,700,135 B2
(45) Date of Patent: Apr. 20, 2010

(54) CEREBRAL PROTECTION WITH A XENON-CONTAINING GAS

(75) Inventors: Peter Neu, Duisburg (DE); Carsten Pilger, Rheurdt (DE); Matthias Reyle-Hahn, Prinz-Friedrich-Leopold-Str. 3, 14129 Berlin (DE)

(73) Assignees: Air Liquide Deutschland GmbH, Duesseldorf (DE); Matthias Reyle-Hahn, Berlin (DE)

( * ) Notice: Subject to any disclaimer, the term of this patent is extended or adjusted under 35 U.S.C. 154(b) by 491 days.

(21) Appl. No.: 11/767,604

(22) Filed: Jun. 25, 2007

(65) Prior Publication Data

US 2008/0206157 A1 Aug. 28, 2008

Related U.S. Application Data

(62) Division of application No. 10/517,723, filed on Dec. 10, 2004, now Pat. No. 7,235,264.

(51) Int. Cl.
*A61K 33/00* (2006.01)
*A01N 59/00* (2006.01)

(52) U.S. Cl. .................................. 424/718; 424/600
(58) Field of Classification Search ................ None
See application file for complete search history.

(56) References Cited

FOREIGN PATENT DOCUMENTS

WO WO 00/53192 * 9/2000

OTHER PUBLICATIONS

FAXed amendments to the specifcation and claims Dec. 11, 2009 5 pages.*

* cited by examiner

*Primary Examiner*—Ernst V Arnold
(74) *Attorney, Agent, or Firm*—Connolly Bove Lodge & Hutz

(57) ABSTRACT

Xenon or xenon-containing gases and, where appropriate, an NO source are employed as medicament for cerebral protection. Cerebral protection is defined as reducing or preventing impairments of cerebral function of various causes, but especially secondary to perfusion impairments of unclear etiology. The medicament can be used for cerebral protection for the prophylaxis of impairments of cerebral perfusion and for therapy after cerebral disorders have occurred, irrespective of the cause (e.g. cognitive, sensory or motor in nature).

12 Claims, No Drawings

CEREBRAL PROTECTION WITH A XENON-CONTAINING GAS

CROSS REFERENCE TO RELATED APPLICATION

The application is a divisional of Ser. No. 10/517,723, filed Dec. 10, 2004 now U.S. Pat. No. 7,235,264, all of the details of which are incorporated herein by reference thereto.

The invention relates to a medicament which comprises xenon and, where appropriate, an NO source.

WO 02/22141 A2 describes the use of xenon or xenon-containing gases as medicament, in particular cardiovascular agent.

DE 19933704 A1 describes the use of a liquid preparation which comprises a lipophilic gas such as xenon for neuroprotection and neuroregeneration.

Neuroprotection and neuroregeneration involves the protection and the regeneration of individual nerve cells by acting on NMDA receptors in the nerve cell. Neuroprotection by modulating the activity of NMDA receptors is also disclosed in U.S. Pat. No. 6,274,633.

An undersupply of oxygen to the brain leads to damage to the brain.

The invention is based on the object of providing an alternative medicament, in particular a medicament for the treatment of cerebral disorders.

It has been found that the oxygen supply in the brain is improved on administration of xenon or xenon-containing gases, in particular by inhalation. In addition, in this way cognitive, sensory and motor conditions and manifestations secondary to oxygen deficiency in the brain are alleviated or even cured.

The invention relates to a medicament for cerebral protection having the features described in claim 1.

Cerebral protection is defined as reducing or preventing impairments of cerebral function of various causes, but especially secondary to perfusion impairments of unclear etiology. The medicament can be used for cerebral protection for the prophylaxis of impairments of cerebral perfusion and for therapy after cerebral disorders have occurred, irrespective of the cause (e.g. cognitive, sensory or motor in nature).

The medicament for cerebral protection protects the brain of humans or mammals from damage, in particular from damage associated with oxygen deficiency. It does not act just on single nerve cells but acts on the brain or on parts. of the brain. The medicament for cerebral protection acts in particular on the blood vessels in the brain. Available results indicate an improvement in cerebral perfusion through administered xenon. According to preliminary results, xenon acts as vasodilator, especially as capillary vasodilator in the capillary vascular system. In addition, according to preliminary results, cerebral autoregulation is maintained or improved. The oxygen supply in the brain is increased.

The invention thus relates further to the use of xenon or of a xenon-containing gas as cerebral vasodilator, preferably as cerebral capillary vasodilator, in particular as cerebral capillary vasodilator in the capillary vascular system.

The invention further relates to the use of xenon or of a xenon-containing gas to produce a medicament for cerebral vasodilatation, preferably to produce a medicament for cerebral capillary vasodilatation, in particular to produce a medicament for cerebral capillary vasodilatation in the capillary vascular system.

Xenon or a xenon-containing gas mixture are further used to produce a medicament for the treatment of impairments of blood flow in the brain, to produce a medicament for the treatment of impairment of cerebral perfusion, to produce a medicament for the treatment of cognitive impairments, to produce a medicament for cerebral protection, to produce a medicament for the prophylaxis and/or therapy of impairments of cognitive performance, also postoperatively, to produce a medicament for the treatment of stroke, to produce a medicament for the prophylaxis of stroke, to produce a medicament for improving the oxygen supply in the brain, to produce a medicament for the treatment of post-ischemia syndrome, to produce a medicament for promoting blood flow in the brain.

In addition, xenon or xenon-containing gas mixtures are advantageously employed as medicament for the treatment of states with oxygen deficiency, especially oxygen deficiency in the brain. For example, xenon or xenon-containing gas mixtures are employed in emergency situations such as the treatment of avalanche victims. Xenon or a xenon-containing gas mixture is also used to produce a medicament for improving the oxygenation of the brain.

Xenon or a xenon-containing gas mixture are further used to produce a medicament for the treatment of cognitive or cerebral dysfunction, in particular of postoperative cognitive dysfunction after cardiac surgical operations, also with use of heart-lung machines (HLM) and cardiac assist systems after general surgical procedures.

Cerebral dysfunctions relate to impairments of the microcirculation, of oxygen utilization and of metabolic functions. The medicament is thus also used to treat cerebral disorders such as impairments of the microcirculation, of oxygen utilization and of metabolic functions.

The medicament effects an increase in the cerebral blood flow and the microcirculation.

The invention thus further relates to the use of xenon or of a xenon-containing gas mixture to produce a medicament for the treatment of cognitive dysfunction, in particular of postoperative cognitive dysfunction. The invention further relates to the use of xenon or of a xenon-containing gas mixture to produce a medicament for the treatment of cerebral dysfunction.

The medicament for cerebral protection and the indications mentioned comprises xenon or a xenon-containing gas mixture. It preferably consists of gaseous xenon or a xenon-containing gas mixture. The medicament consists for example of xenon gas, a gas mixture of xenon and oxygen or a gas mixture of xenon, oxygen and an inert gas.

The medicament for cerebral protection and the indications mentioned (referred to as the medicament for short) is preferably gaseous, in particular it contains no solid or liquid constituents on administration, and is thus preferably in the form of a pure gas phase on administration. The medicament for cerebral protection and the indications mentioned is preferably administered by inhalation through the lungs. The medicament is also administered by means of a heart-lung machine. The medicament is preferably used for treating humans.

The medicament for cerebral protection and the indications mentioned is usually provided as pure gaseous xenon. It may also be provided as gas mixture. The medicament is usually employed as a gas mixture which maintains respiration and which comprises xenon and oxygen. Such gas mixtures are employed for example in emergency medicine, where gas-mixing or gas-metering devices are too complicated for mobile use.

Gaseous xenon or xenon-containing gas mixtures are particularly advantageously employed for prophylaxis. Prophylactic administration of xenon or xenon-containing gas mixtures takes place for example preoperatively, intraoperatively or postoperatively.

The provided medicament for cerebral protection and the indications mentioned, or the medicament produced directly on use, in particular in the direct vicinity of the patient, is for example a gas mixture which comprises from 1 to 80% by volume (based on standard conditions, i.e. 20° C., 1 bar absolute) xenon (e.g. remainder oxygen). The medicament which is administered to the patient comprises xenon in pharmacologically or therapeutically effective amount, in particular in subanesthetically or anesthetically effective amount. A medicament with xenon in subanesthetically effective amount is advantageous. Subanesthetically effective (subanesthetic) amounts of xenon mean those amounts or concentrations of xenon which are insufficient for general anesthesia. These are in general amounts of up to 70% by volume xenon, preferably up to 65% by volume, particularly preferably up to 60% by volume, in particular up to 50% by volume xenon. Pure xenon is accordingly metered into the patient's respiratory gas in the stated concentrations. This means that the respiratory gas supplied to the patient comprises for example from 5 to 60% by volume, 5 to 50% by volume, 5 to 40% by volume, 5 to 30% by volume or 5 to 20% by volume xenon. In special cases, e.g. for prophylaxis, especially during prolonged ventilation, a dosage of xenon in the respiratory gas with a low concentration, for example 1 to 35% by volume, 5 to 25% by volume or 5 to 20% by volume xenon in the respiratory gas, may be advantageous.

The medicaments, in particular gaseous medicaments, preferably comprise besides xenon one or more gases or substances which are gaseous at body temperature under atmospheric pressure. Examples of gas mixtures which can be used are xenon-oxygen gas mixtures or gas mixtures of xenon and one or more inert gases such as nitrogen or a rare gas or xenon-oxygen inert gas gas mixtures. Admixture of a gas to the xenon may be very advantageous if it is intended to introduce little xenon into the body.

Examples of gases or gas mixtures employed as medicament for cerebral protection: 1.) 100% by volume xenon; 2.) 70% by volume xenon/30% by volume oxygen; 3.) 65% by volume xenon/30% by volume oxygen/5% by volume nitrogen; 4.) 65% by volume xenon/35% by volume oxygen; 5.) 60% by volume xenon/30% by volume oxygen 10% by volume nitrogen; 6.) 60% by volume xenon/35% by volume oxygen/5% by volume nitrogen; 7.) 60% by volume xenon/40% by volume oxygen; 8.) 55% by volume xenon/25% by volume oxygen/20% by volume nitrogen; 9.) 55% by volume xenon/30% by volume oxygen/15% by volume nitrogen; 10.) 55% by volume xenon/35% by volume oxygen/10% by volume nitrogen; 11.) 55% by volume xenon/40% by volume oxygen/5% by volume nitrogen; 12.) 55% by volume xenon/45% by volume oxygen; 13.) 50% by volume xenon/50% by volume oxygen; 14.) 50% by volume xenon/45% by volume oxygen/5% by volume nitrogen; 15.) 50% by volume xenon/40% by volume oxygen/10% by volume nitrogen; 16.) 50% by volume xenon/30% by volume oxygen/20% by volume nitrogen; 17.) 50% by volume xenon/25% by volume oxygen/25% by volume nitrogen; 18.) 45% by volume xenon/55% by volume oxygen; 19.) 45% by volume xenon/50% by volume oxygen/5% by volume nitrogen; 20.) 45% by volume xenon/45% by volume oxygen/10% by volume nitrogen; 21.) 45% by volume xenon/40% by volume oxygen/15% by volume nitrogen; 22.) 45% by volume xenon/35% by volume oxygen/20% by volume nitrogen; 23.) 45% by volume xenon/30% by volume oxygen/25% by volume nitrogen; 24.) 45% by volume xenon/30% by volume oxygen/25% by volume nitrogen; 25.) 40% by volume xenon/30% by volume oxygen/30% by volume nitrogen; 26.) 40% by volume xenon/50% by volume oxygen/10% by volume nitrogen; 27.) 35% by volume xenon/25% by volume oxygen/40% by volume nitrogen; 28.) 35% by volume xenon/65% by volume oxygen; 29.) 30% by volume xenon/70% by volume oxygen; 30.) 30% by volume xenon/50% by volume oxygen/20% by volume nitrogen; 31.) 30% by volume xenon/30% by volume oxygen/40% by volume nitrogen; 32.) 20% by volume xenon/80% by volume oxygen; 33.) 20% by volume xenon/30% by volume oxygen/50% by volume nitrogen; 34.) 15% by volume xenon/30% by volume oxygen/55% by volume nitrogen; 35.) 15% by volume xenon/50% by volume oxygen/35% by volume nitrogen; 36.) 10% by volume xenon/90% by volume oxygen; 37.) 10% by volume xenon/50% by volume oxygen/40% by volume nitrogen; 38.) 10% by volume xenon/30% by volume oxygen/60% by volume nitrogen; 39.) 10% by volume xenon/25% by volume oxygen/65% by volume nitrogen; 40.) 5% by volume xenon/25% by volume oxygen/70% by volume nitrogen; 41.) 5% by volume xenon/30% by volume oxygen/65% by volume nitrogen; 42.) 5% by volume xenon/50% by volume oxygen/45% by volume nitrogen; 43.) 5% by volume xenon/30% by volume oxygen/65% by volume nitrogen; 44.) 5% by volume xenon/95% by volume oxygen; 45.) 1% by volume xenon/99% by volume oxygen; 46.) 1% by volume xenon/30% by volume oxygen/69% by volume nitrogen; 47.) 1% by volume xenon/25% by volume oxygen/74% by volume nitrogen.

The medicament, especially the medicament for cerebral protection, is particularly advantageously employed in intensive-care medicine, especially when the medicament must be administered over a prolonged period, for example during long-term ventilation. In this case, the medicament has the particular advantage according to the current state of knowledge of having no side effects because the medicament itself is not metabolized by the body. Thus, on use of xenon or xenon-containing gases as medicament, no metabolites are formed in the body, and no accumulation of the medicament in the body occurs.

Xenon is administered, especially during long-term ventilation and for prophylaxis, advantageously in subanesthetically effective concentrations in a breathable gas (respiratory gas). Administration of breathable gases with a content of from 5 to 45% by volume xenon, preferably 5 to 40% by volume xenon, is advantageous especially during long-term ventilation. The breathable gas during long-term ventilation has for example a content of from 20 to 30% by volume oxygen, it being possible to increase the oxygen content if required at times for example to 30 to 95% by volume oxygen. The remaining gas in the breathable gas usually consists of nitrogen or another inert gas.

The employed xenon gas generally has the natural isotope composition. The isotope composition of the xenon may differ from the natural isotope composition, in particular on use for diagnostic purposes. The xenon gas is preferably employed in high purity, as usual for medical gases. The xenon gas is preferably used as pure gas or mixed with other gases to produce a gaseous medicament for the applications mentioned.

Gaseous xenon (pure xenon) is generally provided as compressed gas in compressed gas containers such as compressed gas cylinders or pressurized cans. It is also possible to provide xenon-containing gas mixtures in compressed gas containers. The gaseous medicament can also be provided in a container as liquefied gas or gas mixture or in cryogenically solidified form.

The medicament is usually administered using a ventilation machine with a gas-metering unit or with an anesthesia machine. The pharmaceutical is advantageously produced from the pure gases immediately before use, for example by mixing xenon, oxygen and, where appropriate, an inert gas (e.g. with the aid of an anesthesia machine) in the direct vicinity of the patient.

The medicament is usually administered as dry, moist gas or water vapor-saturated gas to the patient.

It is advantageous further to combine the xenon-containing medicament with a medicament which comprises an NO source, preferably for the treatment or prophylaxis of cerebral disorders, in particular for use for cerebral protection.

The invention thus further relates to a medicament comprising xenon and an NO source or a xenon-containing gas mixture and an NO source, where xenon and NO source are present in pharmacologically effective concentration.

The invention further relates to a combination product for simultaneous, separate or sequential use of xenon and an NO source or a xenon-containing gas and an NO source.

The invention relates in particular to a medicament consisting of an inhalable medicament comprising xenon or a xenon-containing gas, and a medicament which is administered preferably orally, by inhalation or parenterally and which comprises an NO source, as combination product for simultaneous, separate or sequential use.

The invention further relates to the use of xenon and of an NO source or a xenon-containing gas and an NO source for the treatment of cerebral disorders, in particular for cerebral protection.

The invention further relates to the use of xenon and of an NO source or a xenon-containing gas and an NO source to produce a medicament for the treatment of cerebral disorders, in particular a medicament for cerebral protection.

The medicament serving as combination product preferably consists of an inhalable medicament comprising xenon or a xenon-containing gas, and of a medicament which is administered orally, by inhalation (e.g. as aerosol) or parenterally and which comprises an NO source.

A nitric oxide source (NO source) is NO (nitric oxide), an NO-containing gas or gas mixture or, preferably, a substance or preparation which releases nitric oxide (NO), stimulates endogenous NO production or inhibits the breakdown of NO in the body. A nitric oxide source are, in particular, NO-releasing and/or NO-forming compounds.

NO sources and, in particular, NO-releasing compounds are described in DE 691 27 756 T2 (e.g. page 8, line 7, to page 9, end of the second paragraph, therein), to which reference is hereby made. Examples of NO-releasing compounds are S-nitroso-N-acetylpienicillamine (SNAP), S-nitrosocysteine, nitroprusside, nitrosoguanidine, glycerol trinitrate, isoamyl nitrite, inorganic nitrite, azide or hydroxylamine. The NO-releasing compounds are introduced into the lung for example by inhalation as aerosol, as described in DE 691 27 756 T2 and to which reference is hereby made.

If it is intended to increase the NO level in the brain on administration of NO-releasing compounds via the blood, this may be prevented by the blood-brain barrier. This problem is circumvented according to WO 00/56328 by administering an agent which stimulates endogenous NO production, such as L-arginine. Substances which increase endogenous NO production are regarded as NO-forming substances. Substances which stimulate endogenous NO production are advantageously employed in combination with NO-releasing compounds. Preceding or simultaneous administration of one or more substances stimulating endogenous NO production improve the ability to deliver the NO-releasing compounds into the brain, leading to an improved efficacy of the NO-releasing compounds in the brain. One or more substances stimulating endogenous NO production, one or more NO-releasing compounds and xenon or a xenon-containing gas are thus advantageously administered at separate times or simultaneously. For example, initially there is administration of a substance stimulating endogenous NO production and, in a further step, NO-releasing compound and xenon are administered. It may also be advantageous to start with administration of xenon by inhalation and, in a further step, to administer the substance stimulating endogenous NO production and an NO-releasing compound, simultaneously or at separate times.

The combination medicament comprises xenon and at least one NO source in therapeutically effective amount. The medicament comprises xenon for example in subanesthetically or anesthetically effective amount. The dosage of the substances stimulating endogenous NO production is described for example in WO 00/56328, to which reference is hereby made. The dosage of NO-releasing compounds for administration as aerosol is described in U.S. Pat. No. 5,485,827, to which reference is hereby made.

Medicaments with xenon and an NO source are generally used for the treatment, prophylaxis or prevention of disorders of the brain, especially for cerebral protection. The invention thus relates to medicament comprising xenon or a xenon-containing gas and an NO source as combination product for simultaneous, separate or sequential use, especially for disorders of the brain in humans.

Xenon or xenon-containing gases and an NO source are used to produce a medicament for the treatment, prophylaxis or prevention of impairments of blood flow in the brain, to produce a medicament for the treatment of impairment of cerebral perfusion, to produce a medicament for the treatment of cognitive impairments, to produce a medicament for cerebral protection, to produce a medicament for the prophylaxis and/or therapy of impairments of cognitive performance, also postoperatively, to produce a medicament for the treatment of stroke, to produce a medicament for the prophylaxis of stroke, to produce a medicament for improving the oxygen supply in the brain, to produce a medicament for the treatment of post-ischemia syndrome, to produce a medicament for promoting blood flow in the brain.

For example, in a case of stroke the medicament is advantageously employed in the following way. Firstly a xenon-containing gas is administered, e.g. in subanesthetically and sedatively effective amount. In a next phase of the sequential administration of the medicament, advantageously a gaseous, liquid or solid preparation with an NO source (one or more substances to increase the NO level in the brain) or a preparation with an NO source in combination with xenon or a xenon-containing gas is administered.

Xenon or a xenon-containing gas mixture and an NO source are further used to produce a medicament for the prophylaxis and/or therapy of impairments of cognitive performance, also postoperatively.

The combination medicament is usually employed as combination of one component (e.g. as inhalable medicament) with xenon and of a further component with an NO source, e.g. a medicament which is administered parenterally, by inhalation or orally and has at least one NO source. The medicament comprises xenon in a pharmacologically or therapeutically effective amount, e.g. in subanesthetically or anesthetically effective amount. The medicament comprises the NO source in a pharmacologically or therapeutically effective amount.

The combination medicament consists for example of xenon, an inert gas and an is NO source or of xenon, oxygen, an inert gas and an NO source.

The invention claimed is:

1. In a method of treating a patient by administering a medicament to the patient during the treatment, the improvement being in that the medicament is a xenon preparation which is provided in a form of a combination medicament comprising a pharmacologically effective concentration of xenon selected from the group consisting of gaseous xenon and a xenon containing gas mixture, and a medicament that comprises a NO-releasing compound, a substance that stimulates endogenous NO production wherein said substance is L-arginine, administering the xenon to a patient in a subanesthetic amount wherein the gaseous xenon or the xenon containing gas mixture administered to the patient contains no more than 70% bay volume of xenon and when the gaseous xenon or xenon containing gas mixture is metered into the patient's respiratory gas so that the combined gas supplied to the patient contains from 5 to 70% by volume xenon, administering the medicament that comprises the NO-releasing compound, the substance that stimulates endogenous NO production, by inhalation or orally and the combination medicament is administered to a patient for a treatment selected from the group consisting of (a) treatment of impairments of blood flow in the brain, (b) treatment of impairment of cerebral perfusion, (c) cerebral protection, (d) treatment of stroke, (e) improving the oxygen supply in the brain, (f) treatment of post-ischemia syndrome, (g) promoting blood flow in the brain, and (h) cerebral vasodilation, and selecting a patient in need of one of said treatments (a) to (h).

2. The method as claimed in claim 1, wherein the NO-releasing compound is selected from the group consisting of S-nitroso-N-acetylpenicillamine (SNAP), S-nitrosocysteine, nitroprusside, nitrosoguanidine, glycerol trinitrate, isoamyl nitrite, inorganic nitrite, and hydroxylamine.

3. The method as claimed in claim 2, wherein the NO-releasing compound is introduced into the lung by inhalation as aerosol.

4. The method as claimed in claim 1, wherein the substance which stimulates endogenous NO production is employed in combination with the NO-releasing compound.

5. The method as claimed in claim 4, wherein the preparation is administered to a patient for a treatment selected from the group consisting of cerebral protection and cerebral vasodilation.

6. The method as claimed in claim 1, wherein the NO-releasing compound is introduced into the lung by inhalation as aerosol.

7. The method as claimed in claim 3, wherein the substances which stimulate endogenous NO production is employed in combination with the NO-releasing compound.

8. The method as claimed in claim 2, wherein the substances which stimulate endogenous NO production is employed in combination with the NO-releasing compound.

9. The method as claimed in claim 1, wherein the substance which stimulates endogenous NO production is employed in combination with the NO-releasing compound.

10. The method as claimed in claim 3, wherein the preparation is administered to a patient for a treatment selected from the group consisting of cerebral protection and cerebral vasodilation.

11. The method as claimed in claim 2, wherein the preparation is administered to a patient for a treatment selected from the group consisting of cerebral protection and cerebral vasodilation.

12. The method as claimed in claim 1, wherein the preparation is administered to a patient for a treatment selected from the group consisting of cerebral protection and cerebral vasodilation.

* * * * *